United States Patent
Li et al.

Patent Number: 5,258,015
Date of Patent: Nov. 2, 1993

[54] LOCKING FILAMENT CAPS

[75] Inventors: Lehmann K. Li, Wellesley; James P. O'Leary, Medford, both of Mass.

[73] Assignee: American Cyanamid Company, Stamford, Conn.

[21] Appl. No.: 695,536

[22] Filed: May 3, 1991

[51] Int. Cl.$^5$ .............................. A61B 17/00
[52] U.S. Cl. .................. 606/232; 128/DIG. 26; 128/912; 24/453; 24/662; 607/126
[58] Field of Search ........... 606/232, 233, 220, 164, 606/165; 24/324, 453, 662, 4; 128/DIG. 26, 912, 785

[56] References Cited

U.S. PATENT DOCUMENTS

| | | | |
|---|---|---|---|
| 3,487,837 | 1/1970 | Petersen | 128/DIG. 26 |
| 3,664,345 | 5/1972 | Dabbs et al. | 606/232 |
| 3,845,772 | 11/1974 | Smith | 606/233 |
| 3,976,079 | 8/1976 | Samuels et al. | 606/232 |
| 4,291,698 | 9/1981 | Fuchs et al. | 606/232 |
| 4,532,926 | 8/1985 | O'Holla | 606/220 |
| 4,688,560 | 8/1987 | Schultz | 606/73 |
| 4,688,561 | 8/1987 | Reese | 128/92 YF |
| 4,705,040 | 11/1987 | Mueller et al. | 128/334 R |
| 4,750,492 | 6/1988 | Jacobs | 606/232 |
| 4,793,031 | 12/1988 | Kasai | 24/324 |
| 4,825,859 | 5/1989 | Lambert | 128/912 |
| 4,890,966 | 1/1990 | Umezawa | 24/453 |
| 4,920,618 | 5/1990 | Iguchi | 24/454 |
| 5,078,731 | 1/1992 | Hayhurst | 606/232 |

*Primary Examiner*—Stephen C. Pellegrino
*Assistant Examiner*—Gary Jackson
*Attorney, Agent, or Firm*—Mark J. Pandiscio; Douglas E. Denninger

[57] ABSTRACT

An improved locking cap for mounting on the smooth flexible filament of a surgical fastener wherein the locking cap is of a thin flat washer-like shape with gripping elements for engaging the filament and locking the cap in position relative to the filament.

40 Claims, 4 Drawing Sheets

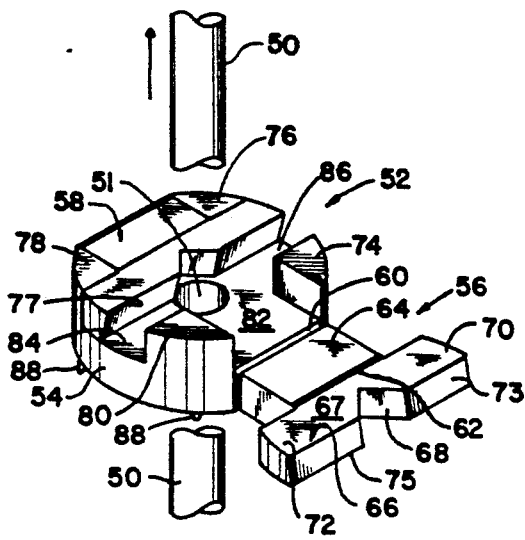
Fig. 4
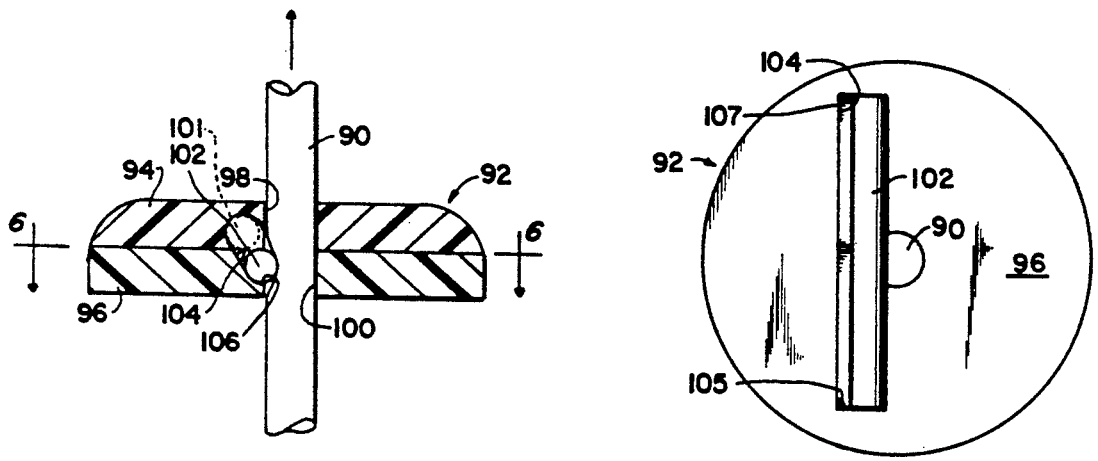
Fig. 5
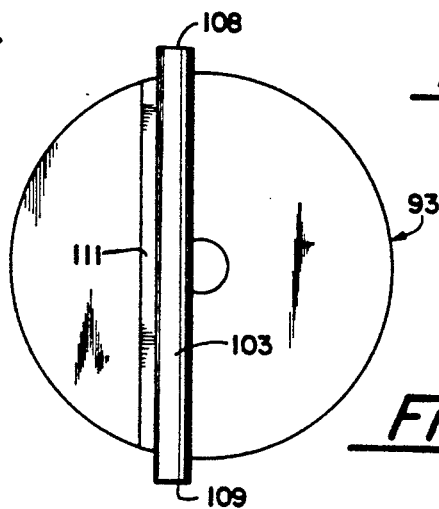
Fig. 6
Fig. 6A

LOCKING FILAMENT CAPS

FIELD OF THE INVENTION

This invention relates to surgical fasteners used to attach two or more tissue members to one another, or a tissue member to a bone, and is more particularly concerned with a means for locking the fastener end elements against the tissue.

BACKGROUND OF THE INVENTION

Surgical fasteners are used to attach two or more tissue members to one another. A typical fastener consists of a relatively thin flexible filament having a relatively rigid, bar-like head on at least one end thereof, wherein the bar-like head normally resides perpendicular to the adjoining length of filament during use. In U.S. Pat. No. 4,669,473, issued on Jun. 2, 1987 to Richards et al., there is shown such a surgical fastener, generally referred to as a "T-bar" type of fastener. The fastener is deployed, for example, by anchoring the fastener's bar-like head in a human bone by means of a special tool, with the filament threaded through the tissues to be joined. The several tissue members may then be captivated on the filament between the fastener head and the end of the filament by tying a knot on the free end of the filament. In U.S. Pat. No. 4,669,473 there is shown a filament which has a plurality of ribs formed along its filament of conical shape, with the large end of each cone closer to the head. An associated washer is slid over the free end of the filament in the direction of the head end and brought to bear against the outermost tissue to be joined. The washer cannot move backwards away from the head end because of the conical nature of the ribs. A related concept is shown in U.S. Pat. No. 4,532,926, issued on Aug. 6, 1985 to O'Holla. Such an arrangement has proven to be costly and disadvantageous in that the body of the filament is required to be specially formed with conical elements. Further, since it may be desired to provide a certain degree of tension between the tissue members or the tissue members and bone, the stepped arrangement provided by the ribbed filament affords only a rudimentary degree of tensioning in predefined incremental amounts. Additionally, slight loosening may occur when the washer is set by the appropriate tool, since there is a tendency for the washer to slip backward to the next outboard conical rib when the washer is set.

Another form of tissue fastener arrangement is shown in European Patent Application Publication No. 0,129,442, published On Dec. 27, 1984, in which a staple type fastener has its legs brought through a bar member and wherein the legs are subsequently permanently deformed or coined to form a bulged out portion within the bar member, not unlike a "pop" rivet. Such a construction requires that metal or other material be used which has no memory, i.e., which can be deformed and which thereafter will not return to its former position. This requirement limits the use of such a construction to special materials which will retain this deformation when a special "setting" tool is removed after the staple is in place. Most materials used in fasteners which are intended to be absorbed by the human body would therefore not be capable of use in this type of staple.

OBJECTS OF THE INVENTION

It is therefore one object of the invention to provide a locking filament cap that may be used with a smooth strand filament of a surgical fastener, and which is locked into position by a clamping action at any point along the filament.

It is a further object of the invention to provide alternative arrangements of filament caps which may be slid along the smooth surface of a filament until reaching the desired point of placement, whereupon portions of the caps are caused to lock to the smooth filament of the suture.

A still further object of the invention is to provide a locking cap for a suture having filament ends which is universal in nature, in that it may be deployed with sutures of various forms which have straight filament ends.

Still another object of the invention is to provide a locking filament cap that is usable with a smooth strand filament surgical fastener, and can retain any desired degree of tensioning between tissue members or between tissue members and bone.

SUMMARY OF THE INVENTION

In accordance with the present invention there is provided a fastener cap which is deployed along the smooth filament of a surgical fastener. The fastener cap may be in one of several forms which provide gripping elements to bear against the filament and which are urged into filament-engaging position, at which time the filament end may be cut flush with the end of the cap. Among the forms of filament caps are those provided with locking flaps attached by living hinges to the cap. In another form a floating rod is used which lies within an angled passage within the cap and which can assume a pinching and gripping position when tension is applied to the filament and subsequently released. In still another form a wedging sleeve is employed which may be placed into anchored position within the cap whereby it bears against the filament to grip it, and is incapable of being withdrawn. An alternate form of such a cap employs a collet having wedging fingers which are caused to grip the filament when an appropriately shaped washer is pushed over the collet. In a further form of the invention a gripping bar or gate is pressed into position into an appropriately shaped recess in the cap and frictionally retained therein as a result of the tension applied to the filament. A method of applying the locking filament cap is also described.

BRIEF DESCRIPTION OF THE DRAWINGS

These and other objects of the invention are described in more detail hereinafter, and are further illustrated in the accompanying drawings, in which:

FIG. 4 is a perspective view of another form of locking filament cap of the invention employing living hinge-mounted clamping elements;

FIG. 5 is a cross-sectional view of still another form of locking filament cap employing a rolling locking rod;

FIG. 6 is a cross-sectional view taken along line 6—6 of FIG. 5;

FIG. 6A is a cross-sectional view similar to FIG. 6 but showing a variation of the locking rod arrangement;

DETAILED DESCRIPTION OF THE INVENTION

Figure 1:
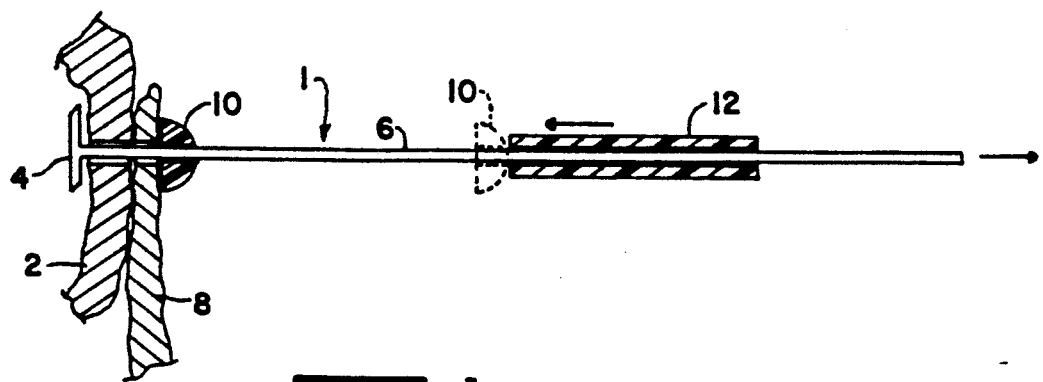
FIG. 1 is a perspective view, partially in cross-section, of the use of a locking filament cap in connection with a "T-bar" suture in an arthroscopic surgery procedure.

The general conception of the application of the invention is shown in FIG. 1, wherein a "T-bar" fastener 1 has its headed end 4 embedded in a bone 2. Extending from the headed end 4 is a smooth filament 6 which passes through the tissue 8 and extends therefrom generally perpendicular to the headed end 4. The locking filament cap 10 has the filament 6 passing through it and an actuator tool 12 is employed which pushes the cap 10 from an initial position (shown in dotted lines) along the filament until it rests against the tissue 8. Tension is then applied to the filament 6 by simply pulling on it in the direction of the arrow. When the appropriate degree of tension is applied the actuator tool 12 is operated to actuate the locking function of the cap 10. Thereafter the filament is severed close to the cap.

By way of example, fastener 1 may be of the sort taught in U.S. Pat. No. 4,669,473, and it may be deployed using an installation tool such as one of the sort taught in that patent. The fastener 1 may be formed out of a resilient polymerized resin with the filament 6 being thin and relatively flexible and the headed end 4 being relatively stiff in accordance with the teachings of U.S. Pat. No. 4,669,473. Where the fastener is to be made absorbable by the body, it may be formed out of a polylactide copolymer or a glycolide copolymer in accordance with the teachings of U.S. Pat. Nos. 3,636,956 and 4,300,565. Where the fastener is to be non-absorbable by the body, it may be formed out of a suitable nylon or polyethylene or carbonate polymer or polyether ester copolymer in accordance with the teachings of U.S. Pat. Nos. 4,300,565 and 4,314,561. As an illustration of the size of the suture in a typical application filament 6 will have a diameter of 0.015 inches and the headed end 4 will have a diameter of 0.030 inches and a length of 0.180 inches. The filament locking cap must be made of a material that is denser than the suture filament material in order to be able to deform it and lock the cap against movement. In many applications the cap may be formed of the same material as the headed end 4.

Alternatively, fastener 1 could be a different sort of fastener, so long as the fastener includes a smooth filament element to which the cap 10 must be affixed.

Figure 2:
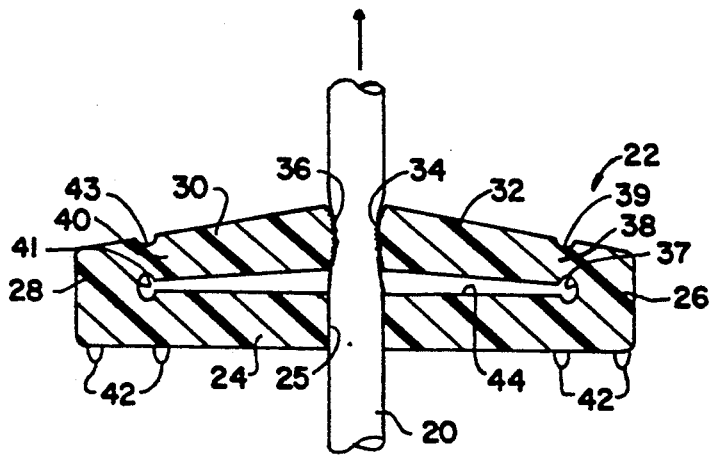
FIG. 2 is a cross-sectional view taken along line 2—2 of FIG. 3, showing one form of locking filament cap of the invention.
Figure 3:
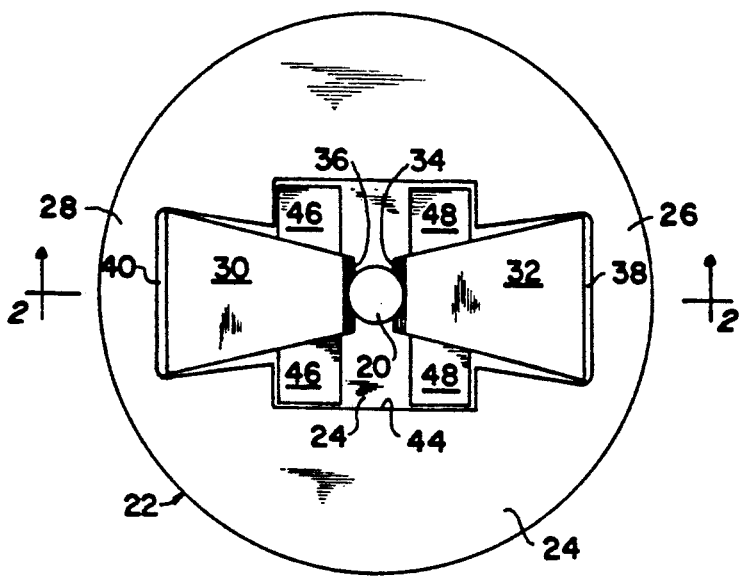
FIG. 3 is a top plan view of the locking filament cap shown in FIG. 2.

In one embodiment of the invention shown in FIGS. 2 and 3 a filament locking cap 22 is shown having a washer-like configuration which employs a "living hinge" construction. The cap 22 is mounted upon a smooth filament 20 of a fastener, wherein the filament will be tensioned by pulling on it in the direction of the arrow shown in FIG. 2. The locking cap 22 is formed with a generally cylindrical shaped base sector 24 provided with a centrally located hole 25 of a diameter which permits passage of the filament 20 with a snug fit. The cap has a recessed area 44 of a shape as shown in FIG. 3 formed to enable a pair of locking flaps 30 and 32 to move therewithin. Extending upwardly from the base sector 24 are first and second arm sector portions 28 and 26, respectively. First locking flap 30 extends from the first arm sector 28, and the second locking flap 32 extends from the second arm sector 26. The arm sectors 28 and 26 are joined to the locking flaps 30 and 32 respectively by respective living hinges 40 and 38. The living hinge 38 is formed by a recessed area 37 at its lower surface and a recessed area 39 at its upper surface. Similarly, the living hinge 40 is formed by a recessed area 41 at its lower surface and a recessed area 43 at its upper surface.

The locking flap 30 is provided with a series of teeth 36 at its innermost extremity and the locking flap 32 is provided with a series of teeth 34 at its innermost extremity. Locking flap 30 is further provided with a stabilizer bar portion 46 extending in opposed directions therefrom as shown in FIG. 3, and locking flap 32 is also provided with a stabilizer in the form of bar portion 48 extending in opposed directions away from flap 32.

When the headed end of the fastener is implanted in bone or body tissue and the filament 20 is drawn through the tissue and extended outwardly from the body, the locking cap 22 is placed on the filament and moved therealong until it contacts the outermost body tissue. The filament is then grasped and placed in tension by pulling it in the direction of the arrow shown in FIG. 2 while an appropriate fastening tool pushes the locking cap firmly against the body tissue. A series of foot members 42 protrude from the lower surface of base sector 24. When the locking cap contacts the body tissue the foot members 42 are pressed into the body tissue to anchor the locking cap against rotation about the filament. The tool then depresses the locking flaps 30 and 32 inwardly so that the series of teeth 34 and 36 are pressed into engagement with the filament 20 (shown in a somewhat exaggerated position in FIG. 2). Upon release of the filament end, the filament, being somewhat resilient, will want to return to its former position. This will apply continuing compressive forces to the flaps 30 and 32 to keep them in the position shown in FIG. 2. Alternatively, even if the filament is not itself somewhat resilient, the tissue engaged by cap 22, having been compressed by the cap and generally being itself somewhat resilient, will cause flaps 30 and 32 to apply continuing compressive forces to filament 6. The stabilizer bars 46 and 48 serve to prevent any cocking of the respective flaps so that the respective series of teeth 36 and 34 are maintained in the most appropriate configuration for engagement with the filament 20.

Another form of locking cap 52 is shown in FIG. 4. The cap 52 is shown as being mounted for use with the filament 50 wherein the filament will be tensioned by pulling on it in the direction of the arrow shown in FIG. 4. In this embodiment the cap 52 is provided with a central hole 51 dimensioned so as to receive the filament 50. The cap 52 is provided with a base sector 54. First and second locking flaps 56 and 58 are hingedly connected to the base sector 54 of the cap 52. These flaps are identical in construction, and only one of them is described in detail hereafter. As shown in FIG. 4, the locking flap 56 is connected to the base sector 54 by means of a living hinge 60 constructed in a manner similar to the living hinges 38 and 40 of the embodiment of FIGS. 2 and 3. However, the locking flap 56 is formed of two arm sectors 64 and 66, which are joined together by a second living hinge 62. The arm sector 66 is longer in extent than sector 64. On the outermost surface 73 of the sector 66 there is provided a V-shaped recess or notch 68. The recess is tapered so that on one surface 67 of the sector 66 the edges of the recess are further apart than the cut out portion on the surface opposite to surface 67 of the sector. Sector 66 is provided with opposed first and second arm extensions 70 and 72, respectively, for a purpose which will become apparent hereafter.

A series of upstanding posts 74, 76, 78 and 80 are provided which protrude from the base sector 54. The surface 82 of the locking cap 52 has an area 84 lying between the posts 78 and 80, and an area 86 lying between the posts 74 and 76. A series of foot members 88 are provided on the lower surface of the base sector 54 for grasping the tissue surface so as to prevent rotation of the locking cap 52 about the filament 50.

When the locking cap 52 is placed on the filament 50 and pushed along it until it seats on body tissue, the locking flaps 56 and 58 are folded on their first living hinges (such as 60 of flap 56) in a manner so that the first arm sectors (such as sector 64 of flap 56) are placed between their adjacent posts (e.g. posts 74 and 80 for flap 56) in a position generally perpendicular to surface 82. The second living hinges of the flaps (such as 62 of flap 56) are thus positioned at a level coordinate with the upper surface of the posts 74, 76, 78 and 80. When the filament is placed in tension by pulling it in the direction of the arrow in FIG. 4, the second arm sectors (such as 66 of flap 56) are then folded over on the second living hinge (such as 62 of flap 56) so that the recesses on the locking flaps (such as 68 on the surface 73) will encompass the filament 50. As shown in FIG. 4 the taper formed by the V-shaped recesses is such that a smaller opening is presented at a level above a larger opening with respect to surface 82 when the flaps 58 and 66 are in the seated position. The surface 73 is also tapered at an inclined angle as shown in FIG. 4 so that the edge 75 of flap 56 is in contact with its complementary edge 77 on flap 58 when the flaps are in clamping position. When the flaps 56 and 58 are pushed downwardly by an appropriate setting tool and the tension which was placed on filament 50 is released, the filament will exert compressive forces on the flaps 56 and 58 to cause the smaller diameter of the tapered recesses to more tightly grip the filament and retain the cap in locked position relative to the filament.

Alternatively, the second hinges (such as hinge 62 of flap 56) may be omitted, and in such event the V-shaped tapered recesses would be formed so that a smaller opening will be presented at a level below a larger opening, with respect to surface 82 when the flaps 58 and 66 are in their seated positions. Should the filament 50 relax and reach a stage where compressive forces on the flaps are reduced to a point that the flaps will have a tendency to rise upwardly away from surface 82, because of the tapered recess arranged as just described, the flaps will be urged to grasp the filament more firmly at the smaller diameter of the tapered recess.

A further embodiment of a locking filament cap is shown in FIGS. 5 and 6, to be used in connection with a filament 90 wherein the filament will be tensioned by pulling it in the direction of the arrow shown in FIG. 5. The locking cap 92 is formed of upper and lower members 94 and 96, respectively, which are bonded together. Aligned central holes 98 and 100 are provided in cap members 94 and 96, respectively, and serve to allow passage of the filament 90. A slot 104 is formed within the cap members 94 and 96 to accommodate a locking rod 102. The slot is internal of the assembled cap 92, and the rod 102 is captured within it to move within the slot 104. When the cap is placed on the filament and moved downwardly therealong as viewed in FIG. 5, the rod 102 will ride up the inclined surface of slot 104 to the uppermost position 101 shown in dotted lines. When tension is applied to filament 90 (by pulling it in the direction of the arrow in FIG. 5) and it is released after the cap 92 is placed into position, the forces applied by the filament will cause the rod 102 to assume the position shown by solid lines in FIG. 5, with the rod bearing against the filament 90. A limit of travel of rod 102 is assured by the lower lip 106 formed by the slot 104.

As shown in FIG. 6 slot 104 is not coterminus with the periphery of locking cap 92, but instead terminates short thereof at end walls 105 and 107. The length of slot 104 is approximately the same as the length of rod 102, but is dimensioned so as to permit rod 102 to freely roll therewithin.

Alternatively, the slot may extend to the periphery of the cap, in which case the rod may be longer than the slot. As shown in FIG. 6A, the slot 111 extends to the periphery of locking cap 93 and the rod 103 extends beyond the cap 93, terminating in end portions 108 and 109. When the cap 93 is set at the desired position against a layer of tissue and the filament is placed under the desired degree of tension, the cap can be locked in place by grasping the end portions 108 and 109 and manually forcing the rod 103 downwardly in slot 111.

Figure 7:
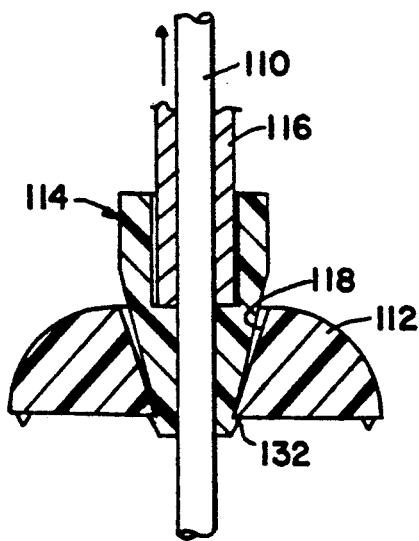
FIG. 7 is a cross-sectional view of a further form of locking filament cap according to the invention.
Figure 8:
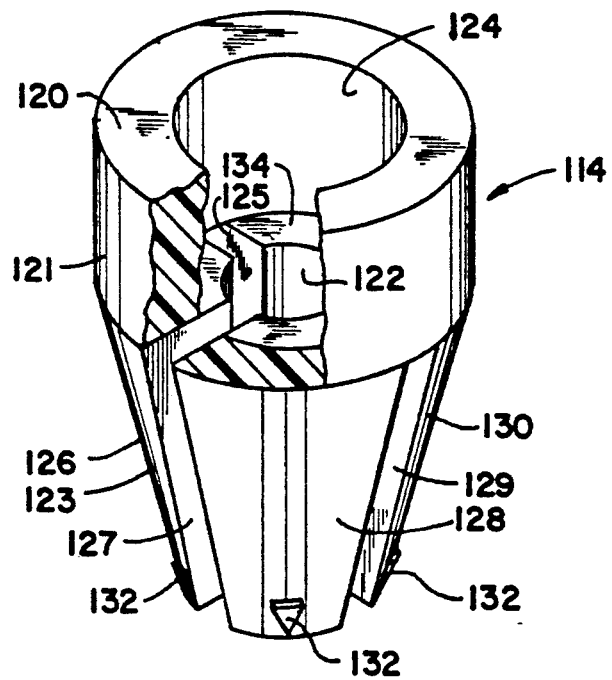
FIG. 8 is a perspective view of the wedging sleeve of the locking filament cap shown in FIG. 7.

A further embodiment of a locking cap is shown in FIGS. 7 and 8 wherein a wedging sleeve 114 is employed in connection with a locking filament cap 112. The cap 112 is formed in a generally washer-like configuration as seen in FIG. 7 and is provided with a centrally located tapered hole 118 shaped to receive the similarly tapered wedging sleeve 114. The wedging sleeve comprises a wedge body 120 which is cylindrically shaped at its upper part 121 and conically shaped at its lower part 123. The body part 123 is provided with a central hole 122 of a diameter enabling passage of the filament 110, wherein the filament will be tensioned by pulling it in the direction of the arrow shown in FIG. 7. The hole 122 extends from an initial recess 124 of larger diameter in the upper body part 121. The recess 124 is of a size which is adapted to receive an actuator tool 116. At the bottom of the recess 124 there is formed a landing area 134, against which the tool 116 is brought to bear. A series of slots 125, 127 and 129 are formed in the lower tapered conical section 123 of the body 120 which divide it into wedging flaps 126, 128 and 130. A series of interlock tabs 132 are provided, one at the lower end of each of the wedging flaps to prevent the sleeve 114 from backing out of the cap 112 once the sleeve is assembled to the cap.

In use the locking cap 112 is placed on the filament 110, and the sleeve 114 is assembled to it but not pushed downward into locking position. The thus loosely assembled cap 112 is pushed along the filament (which has been tensioned by pulling it in the direction of the arrow shown in FIG. 7) until it reaches the tissue surface. Further pressure by the tool 116 will cause the cap 112 to be locked in place on the filament, since pressure on sleeve 114 moves it further into the tapered hole 118 to in turn increase the pressure on the wedging flaps to push them into contact more firmly with the filament 110, and to allow the interlocking tabs to be seated.

Figure 9:
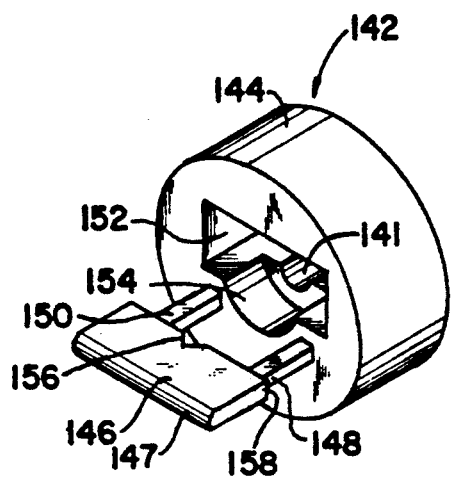
FIG. 9 is a perspective view of a further embodiment of a locking filament cap of the invention shown in open position.
Figure 10:
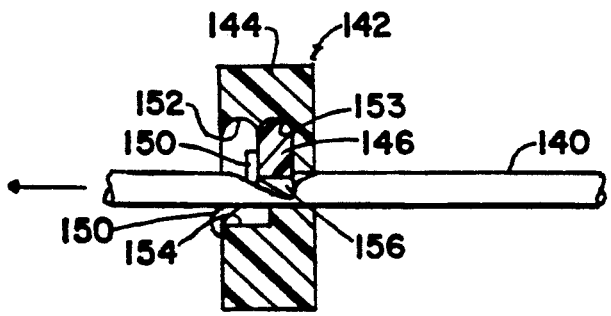
FIG. 10 is a cross-sectional view showing the locking filament cap of FIG. 9 in closed position.

Another embodiment of the teaching of the invention is shown in FIGS. 9 and 10. The filament cap 142 is of cylindrical shape and has a through hole 141 to accommodate the filament 140, wherein the filament will be tensioned by pulling it in the direction of the arrow shown in FIG. 10. The body 144 of the cap 142 has a portion removed to provide a recessed area 152. A locking flap 146 is formed integrally with the body 144 and attached thereto by arms 148 and 150. The outer surface 147 of flap 146 is preferably formed in a curved shape to cooperate with a similarly shaped surface 153 in the recessed area 152 of the cap to permit the locking flap 146 to be retained in locked position. A lower recessed portion 154 is provided in the area 152 to accommodate a setting tool for moving and locking the flap 146. When the cap 142 is moved along the filament 140 and against the tissue, the flap is positioned into the opening of recess 152. The setting tool is then used to seat the flap into locked position wherein the surfaces 147 and 153 are in mating position, or as nearly so as possible. The notch 156 on the inner surface 158 of flap 146 is of V-shape so as to provide a gripping arrangement for the filament 140 when cooperating with the surface which defines the walls forming the hole 141. The surface 158 is tapered to provide a leading edge 159.

Figure 11:
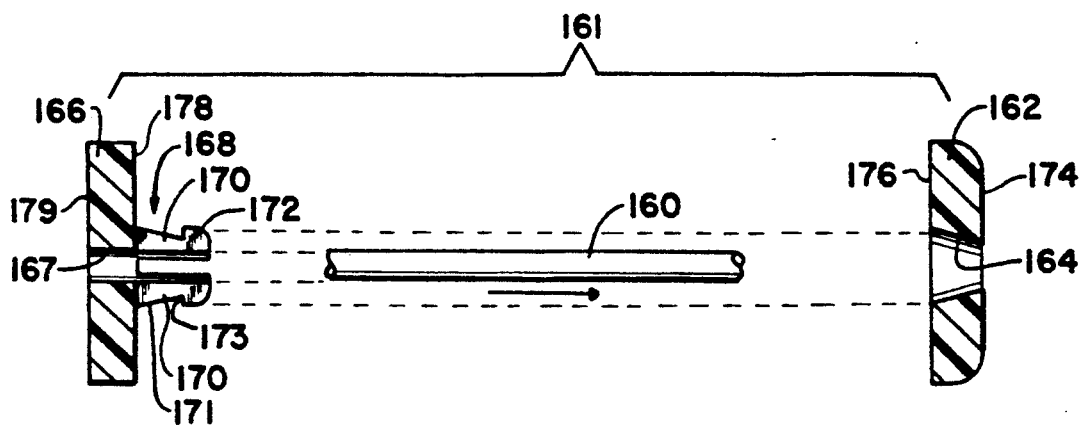
FIG. 11 is a perspective view of still another embodiment of the invention employing a collet-washer combination.

A still further embodiment of the invention is shown in FIG. 11. The locking cap 161 comprises two elements, a collet 166 and a washer 162. The collet 166 is provided with a central hole 167 to permit the passage of the filament 160, wherein the filament will be tensioned by pulling it in the direction of the arrow shown in FIG. 11. The collet is of generally flat cylindrical shape and is provided with a locking extension 168. The extension is furcated to form a series of locking flaps 170 (four being a convenient arrangement). Each flap 170 has a tapered surface 171 which leads to a tab 172 extending normal to the flap 170. Each tab 172 has an inner surface 173 against which the washer 162 may bear. The washer 162 has opposed surfaces 174 and 176 and a central tapered hole 164. The washer 162 is assembled to the collet by being forced over the tabs 172 so that the washer surface 174 rests against the surface 173 of the tabs 172. In use, the separated collet 166 and washer 162 are placed on the filament 160, the filament is tensioned by pulling it in the direction of the arrow shown in FIG. 11, and then the collet is moved toward the tissue, with the collet surface 179 being placed against the tissue. In order to lock the cap 161 to the filament 160, the washer 162 is moved into engagement with the collet so that the surface 176 of washer 162 approaches the surface 178 of the collet. This causes flaps 170 to engage filament 160 and thereby hold the cap in place along the filament, with tabs 172 preventing the washer from separating from the collet.

Although what have been described are preferred embodiments of the invention, it is to be appreciated that various modifications may be made without departing from the spirit and scope of the invention.

What is claimed is:

1. A combination of a surgical fastener having a fastener end and a locking cap means for securing the fastener end against tissue, the combination comprising:
   a surgical fastener having a fastener end,
   a cap body having a through passage adapted to receive said fastener end and allowing for translational movement of the cap body with respect to the fastener end,
   means associated with said cap body providing at least one locking member which is movable into a clamping position wherein said member temporarily deforms said fastener end to insure positive clamping but which if moved out of the clamping position allows the fastener end to return to its non-deformed condition,
   and wherein said fastener end is of such material that when tensioned and released it will exert pressure to maintain the locking member in clamping position.

2. The locking cap means of claim 1 wherein the means associated with said cap body provides at least two locking flag elements connected to said cap body by means of a living hinge.

3. The locking cap means of claim 2 wherein said locking flap elements have end portions which are arranged to lie opposed to each other adjacent said through passage.

4. The locking cap means of claim 3 wherein said end portions are each provided with a plurality of teeth.

5. The locking cap means of either of claims 3 or 4 wherein said locking flap elements are each provided with a stabilizer element extending normal to the path of motion of said flap elements.

6. The locking cap means of claim 5 wherein said cap body has a recessed area within which said flap and stabilizer elements are accommodated.

7. The locking cap means of claim 2 wherein said cap body is provided with a series of upstanding post members spaced from one another to provide recessed areas to accommodate said locking flaps.

8. The locking cap means of claim 7 wherein said locking flap elements have end portions which are arranged to lie opposed to each other adjacent said through passage.

9. The locking cap means of claim 8 wherein said end portions are provided with recessed areas juxtaposed to one another at said through passage and of a generally V-shape to accommodate said filament.

10. The locking cap means of claim 9 wherein said recessed areas on said end portions are tapered so that openings are presented on the upper and lower surfaces of the flap elements which are of different depth.

11. The locking cap means of claim 3 wherein each of said flap elements have a second living hinge located intermediate said first living hinge and the end portion.

12. The locking cap means of claim 1 wherein the means associated with said cap body comprises a locking rod movable within said cap body into a clamping position wherein a portion of the rod bears against the fastener end to deform it and insure a positive clamping action.

13. The locking cap means of claim 12 wherein said cap body is provided with a slot dimensioned so as to receive said locking rod in a rolling fit, said slot being angled to said fastener end so as to direct said rod toward the fastener end.

14. The locking cap means of claim 13 wherein said slot is internal of the cap body whereby said rod is captured within said cap body.

15. The locking cap means of claim 13 wherein said slot passes through said cap body substantially chordal to said through passage, and said rod is of a length that exceeds the length of said slot whereby portions of said rod protrude from said cap body.

16. The locking cap means of claim 1 wherein the means associated with said cap body comprises a wedging sleeve providing a plurality of wedging flaps which are movable into a clamping position with said fastener end.

17. The locking cap means of claim 16 wherein said cap body is provided with a tapered hole into which said wedging sleeve is adapted to be placed, said wedging sleeve and tapered hole being so constructed and arranged that as said sleeve is moved further into said tapered hole greater pressure is applied to said wedging flaps to urge them into clamping position.

18. The locking cap means of claim 17 wherein each of said wedging flaps is provided with interlocking means on its outer surface so constructed and arranged that when said wedging sleeve is assembled to said cap body it is prevented from backing out of the cap body.

19. The locking cap means of any of claims 16, 17 or 18 wherein said wedging sleeve comprises an upper cylindrical body having a conical lower portion depending therefrom, said conical lower portion being furcated to form said wedging flaps.

20. The locking cap means of claim 1 wherein the means associated with said cap body comprises a locking flap and a recessed area in said cap body adapted to receive said flap when it is in clamping position with respect to said fastener end.

21. The locking cap means of claim 20 wherein said locking flap is assembled to said cap body by means of attaching arms.

22. The locking cap means of either of claims 20 or 21 wherein said locking flap has an inner end surface which is adapted to bear against said fastener end, said inner end surface having an area cut out in the form of a V-notch to receive the fastener end.

23. A method for securing tissue after a surgical procedure, wherein a surgical suture is employed having a smooth flexible filament end, comprising the steps of passing said filament end through said tissue and extending it outwardly thereof;

mounting a locking cap means upon said filament, said locking cap means having a through hole permitting said locking cap to slide along said filament;

sliding said locking cap means along said filament until said means are in contact with the tissue;

applying pressure against said locking cap means to firmly seat it against the tissue;

thereafter applying tensioning force to said filament while maintaining the pressure upon said locking cap means; and simultaneously actuating clamping elements associated with said locking cap means into filament engaging position, whereby said filament is deformed and said clamping elements are retained in clamping position.

24. The method of claim 23 including the step of severing the filament beyond said locking cap means away from said tissue following said actuating step, whereby said filament thereafter exerts forces to retain said clamping elements in filament engaging position.

25. A locking cap means for securing the fastener end of a surgical fastener against tissue, comprising:

a cap body having a through passage adapted to receive the fastener end and allowing for translational movement of the cap body with respect to the fastener end;

means associated with said cap body providing at least one locking member which is movable into a clamping position wherein said member temporarily deforms the fastener end to insure positive clamping but which if moved out the clamping position allows the fastener end to return to its non-deformed condition;

the cap body being in the form of a collet comprising a generally flat cylindrical portion having a locking extension protruding outwardly therefrom, the through passage being located to pass through both said cylindrical portion and locking extension; and wherein the locking extension is furcated to form a plurality of locking flaps.

26. The locking cap means of claim 25 wherein the means associated with said cap body comprises a washer-like element having a hole centrally thereof.

27. The locking cap means of claim 26 wherein the locking extension has a tapered outer surface, and the hole in said washer-like element is tapered.

28. The locking cap means of claim 25 wherein the locking extension has a tapered outer surface, and the hole in said washer-like element is tapered, whereby when said washer-like element is assembled to said locking extension with the tapered hole in said element being oriented to conform with the tapered outer surface of said locking extension, movement of the washer-like element inward along said locking extension toward the flat cylindrical portion of said collet will force said locking flaps into engagement with said fastener end.

29. The locking cap means of claim 28 wherein said locking flaps each have a protrusion at the end thereof to prevent inadvertent disassembly of said washer-like element from said collet.

30. A locking cap means for securing the fastener end of a surgical fastener against tissue, comprising:

a cap body having a through passage adapted to receive the fastener end and allowing for translational movement of the cap body with respect to the fastener end;

the cap body being in the form of a collet comprising a generally flat cylindrical portion having a locking extension protruding outwardly therefrom, the through passage being located to pass through both said cylindrical portion and locking extension; and the means associated with said cap body comprises a washer-like element having a hole centrally thereof.

31. The locking cap means of claim 30 wherein the locking extension has a tapered outer surface, and the hole in said washer-like element is tapered.

32. The locking cap means of claim 30 wherein the locking extension is furcated to form a plurality of locking flaps.

33. The locking cap means of claim 32 wherein the locking extension has a tapered outer surface, and the hole in said washer-like element is tapered, whereby when said washer-like element is assembled to said locking extension with the tapered hole in said element being oriented to conform with the tapered outer surface of said locking extension, movement of the washer-like element inward along said locking extension toward the flat cylindrical portion of said collet will force said locking flaps into engagement with said fastener end.

34. The locking cap means of claim 33 wherein said locking flaps each have a protrusion at the end thereof to prevent inadvertent disassembly of said washer-like element from said collet.

35. A combination of a surgical fastener having a smooth surface flexible filament and a locking cap means mounted on the smooth surface flexible filament for clamping against tissue, the combination comprising:
- a surgical fastener having a smooth surface flexible filament;
- a cap body having a hole therethrough for receiving said filament and dimensioned to permit translational movement of the cap body with respect to the filament;
- means associated with said cap body providing at least one locking member which is movable into a clamping position wherein said member temporarily deforms said filament to insure positive clamping but which if moved out of the clamping position allows the filament to return to its non-deformed condition; and
- said filament being of such material that when it is tensioned and released it will exert pressure to maintain the locking member in clamping position.

36. A combination of a surgical fastener having a fastener end and a locking cap means for securing the fastener end against tissue, the combination comprising:
- a surgical fastener having a fastener end;
- a cap body having a through passage adapted to receive said fastener end and dimensioned to permit translational movement of the cap body with respect to the fastener end;
- means associated with said cap body providing at least one locking member which is movable into a clamping position wherein said member temporarily deforms said fastener end to insure positive clamping but which if moved out of the clamping position allows the fastener end to return to its non-deformed condition, said locking member being formed of a material denser than the material of said fastener end; and
- said fastener end being of such material that when it is tensioned and released it will exert pressure to maintain the locking member in clamping position.

37. A combination of a surgical filament having a filament end and a locking cap for securing the filament end against tissue, the combination comprising:
- a surgical filament having a filament end;
- a locking cap having a first body and a second body, said first body having a first through passage adapted to receive the filament end to allow translational movement of said first body with respect to the filament end, said first body having at least two locking members mounted proximate said through passage and movable into a clamping position to engage the filament end; and
- said second body having a second, larger-width through passage slideable over an outer portion of said locking member to force it into said clamping position.

38. The locking cap of claim 37 wherein one of an outer surface of said locking member and the second passage of said second body is tapered to drive said locking member into said clamping position.

39. The locking cap of claim 37 wherein said locking member includes tab means for engaging said second body to secure said second body relative to said first body.

40. A locking cap means for securing the fastener end of a surgical fastener against tissue, comprising:
- a first body having a first through passage adapted to receive the fastener end to allow translational movement of said first body with respect to the fastener end, said first body having at least tow locking members spaced about a portion of said through passage and movable into a clamping position to engage the fastener end;
- a second body having a second, larger-width through passage slideable over an outer portion of said locking members to force them into said clamping position;
- at least one of an outer surface of said locking members and the second passage of said second body being tapered to drive all of said locking members into said clamping position; and
- at least one of said clamping members including tab means for engaging said second body to secure said second body relative to said first body.

* * * * *

UNITED STATES PATENT AND TRADEMARK OFFICE
CERTIFICATE OF CORRECTION

PATENT NO. : 5,258,015
DATED : Nov. 2, 1993
INVENTOR(S) : Li et al

It is certified that error appears in the above-indentified patent and that said Letters Patent is hereby corrected as shown below:

```
Col. 8, Line 16, "flag" should read --flap--;
                 and
Col. 12, Line 30, "tow" should read --two--.
```

Signed and Sealed this

Third Day of May, 1994

*Attest:*

BRUCE LEHMAN

*Attesting Officer*     *Commissioner of Patents and Trademarks*